United States Patent
O'Brien et al.

(10) Patent No.: US 12,365,640 B2
(45) Date of Patent: Jul. 22, 2025

(54) LOW TEMPERATURE MEMBRANE PROCESS FOR BIOGAS UPGRADING

(71) Applicant: Air Products and Chemicals, Inc., Allentown, PA (US)

(72) Inventors: Matthew P. O'Brien, House Springs, MO (US); Paul W. Kramer, Ellisville, MO (US)

(73) Assignee: Air Products and Chemicals, Inc., Allentown, PA (US)

( * ) Notice: Subject to any disclaimer, the term of this patent is extended or adjusted under 35 U.S.C. 154(b) by 49 days.

(21) Appl. No.: 18/237,000

(22) Filed: Aug. 23, 2023

(65) Prior Publication Data

US 2025/0066272 A1    Feb. 27, 2025

(51) Int. Cl.
  *C07C 7/05*     (2006.01)
  *C07C 7/00*     (2006.01)
  *C07C 7/144*    (2006.01)

(52) U.S. Cl.
  CPC .............. *C07C 7/005* (2013.01); *C07C 7/144* (2013.01)

(58) Field of Classification Search
  CPC ... C07C 7/005; C07C 7/144; B01D 2256/245; B01D 2257/504; B01D 2257/80; B01D 2258/05; B01D 53/225; B01D 53/226
  See application file for complete search history.

(56) References Cited

U.S. PATENT DOCUMENTS

| | | |
|---|---|---|
| 5,259,869 A | 11/1993 | Auvil et al. |
| 8,317,899 B2 | 11/2012 | Jeffers et al. |
| 10,005,023 B2 | 6/2018 | Burgers et al. |
| 10,258,921 B2 | 4/2019 | Fukuda et al. |
| 2017/0304769 A1 | 10/2017 | Bigeard et al. |
| 2018/0251694 A1 | 9/2018 | Foody et al. |
| 2022/0203294 A1 | 6/2022 | Myrick |

FOREIGN PATENT DOCUMENTS

| | | |
|---|---|---|
| EP | 2588217 | 2/2017 |
| EP | 3240620 | 5/2021 |

OTHER PUBLICATIONS

D.L. MacLean, et al., "Foundamentals of gas permeation", Hydrocarbon Processing, vol. 62, p. 47-51, 1983.
Lloyd M. Robeson, "The upper bound revisited", Journal of Membrane Science, 320, p. 390-400, 2008.

*Primary Examiner* — Thuan D Dang
(74) *Attorney, Agent, or Firm* — Amy Carr-Trexler

(57) ABSTRACT

A method for separating a raw feed gas stream utilizes a compressor, a chiller, a membrane drying stage, and a plurality of membrane separation stages. The raw feed gas stream may comprise biogas. In one example, the raw feed gas stream is supplied to the chiller where it is cooled to a target operating temperature to separate out condensed water. The gas stream is then supplied to a membrane drying stage to separate out water vapor. An off-gas from one of the membrane module stages may be recycled as a low pressure sweep gas on the low pressure side of the membrane drying stage to increase the driving force for water permeation within the membrane drying stage. The gas stream is then supplied to the plurality of membrane separation stages where it is upgraded into a high purity methane stream.

12 Claims, 4 Drawing Sheets

LOW TEMPERATURE MEMBRANE PROCESS FOR BIOGAS UPGRADING

BACKGROUND

This application relates to a multi-stage membrane process and system for methane recovery from biogas. Multi-stage membrane systems are known for upgrading raw biogas streams into high purity methane streams. Current upgrading systems generate a pressurized feed gas stream by supplying a gas stream to a compressor. The compressed gas stream is fed to subsequent membrane separation stages where it is separated into a non-permeate stream that is enriched in a slow gas and a permeate stream that is enriched in a fast gas to recover a final product stream having a high concentration of the slow non-permeating gas, such as methane. Membrane systems often operate at ambient or warmer temperatures chosen to provide a few degrees of superheat to prevent condensation on the membrane materials. Such multi-stage membrane systems can achieve high methane recovery and purity, but often require relatively high capital expenditures (CapEx) associated with high membrane areas (or counts), and high operational expenditures (OpEx) associated with high compressor power costs. Also, operating expenditures for such current upgrading systems can be relatively high due to high recycle flow rates requiring larger and more expensive compressors.

Therefore, there is a need for an effective, reliable, and cost-efficient multi-stage membrane method and system that can achieve a desired methane product recovery and purity while reducing the overall capital and operating expenditures.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Several aspects of the systems and methods are outlined below.

The disclosed embodiments satisfy the need in the art by providing a multi-stage membrane method and system for methane recovery from biogas that reduces the overall cost of ownership and operation. It has been found that systems having polymeric membranes with high carbon dioxide ("CO2") permeability, low CO2 activation energy, and high methane ("CH4") activation energy can be operated at low temperature to exploit the higher CO2/CH4 selectivity while maintaining a high CO2 permeability, which may displace some high selectivity membranes that typically have a low CO2 permeability. In this manner, recycle flow is reduced (which reduces required compressor power) and membrane counts are reduced. Also, to protect the separation membranes from liquid condensation, a chiller and membrane drying stage are provided upstream from the separation membranes. The membrane drying stage may be swept with a portion of a recycled gas from one of the separation membranes. This design flexibility is not available to current separation membrane systems having minimal temperature sensitivity.

Several aspects of the systems and methods are outlined below.

Aspect 1: A method comprising:
(a) compressing a feed gas stream to form a pressurized feed gas stream, the pressurized feed gas stream comprising CH4 and being fully saturated with water;
(b) cooling the pressurized feed gas stream in a chiller to a target operating temperature to form a condensed water stream and a saturated gas stream;
(c) feeding the saturated gas stream to at least one membrane drying stage, each of the at least one membrane drying stage having a high pressure side and a low pressure side, the high pressure side extending from a feed port to a non-permeate port, the low pressure side being in fluid flow communication with a sweep port and a permeate port;
(d) separating the saturated gas stream in the at least one membrane drying stage to form a water vapor permeate stream and a dried gas stream, the dried gas stream having a water content of less than 2,000 ppm;
(e) sweeping and discharging the water vapor permeate stream from the low pressure side using a sweep gas stream that is fed in a direction of flow that is countercurrent to the direction of flow of the saturated gas stream fed into the at least one membrane drying stage in step (c);
(f) separating the dried gas stream in a first separation stage into a first non-permeate stream and a first permeate stream, the first non-permeate stream having a greater percentage of methane than the first permeate stream, the first separation stage comprising at least one first stage membrane module;
(g) separating the first non-permeate stream in a second separation stage into a second non-permeate stream and the sweep gas stream, the second non-permeate stream having a greater percentage of methane than the sweep gas stream, the second separation stage comprising at least one second stage membrane module;
(h) separating the first permeate stream in a third separation stage into a third non-permeate stream and a third permeate stream, the third non-permeate stream having a greater percentage of methane than the third permeate stream, the third separation stage comprising at least one third stage membrane module;
(i) combining the third non-permeate stream and the water vapor permeate stream, and, optionally, a first portion of the sweep gas stream to form a recycle stream; and
j) combining the recycle stream with the feed gas stream before performing step (a);
wherein the target operating temperature is between 0 and 20 degrees C.

Aspect 2: The method of Aspect 1, wherein the target operating temperature is between 3 and 7 degrees C.

Aspect 3: The method of Aspect 1, wherein the target operating temperature is about 5 degrees C.

Aspect 4: The method of Aspect 1, wherein the feed gas stream comprises at least 40% CH4.

Aspect 5: The method of Aspect 1, wherein each of the at least one first stage membrane module has a first stage CO2/CH4 selectivity that is greater than a second stage CO2/CH4 selectivity of each of the at least one second stage membrane module and a third stage CO2/CH4 selectivity of each of the at least one third stage membrane module.

Aspect 6: The method of Aspect 1, wherein each of the at least one first stage membrane module has a first stage CO2/CH4 selectivity greater than 30 at the target operating temperature.

Aspect 7: The method of Aspect 1, wherein each of the at least one second stage membrane module has a CO2/CH4 selectivity greater than 20 at the target operating temperature.

Aspect 8: The method of Aspect 1, wherein each of the at least one first stage membrane module comprises a polymer membrane having a first capacity, and wherein each of the at least one second stage membrane module and each of the at least one third stage membrane module comprises a polymer membrane having a capacity that is greater than the first capacity.

Aspect 9: The method of Aspect 1, wherein each of the at least one first stage membrane module comprises a polymer membrane having a first selectivity, and wherein each of the at least one second stage membrane module and each of the at least one third stage membrane module comprises a polymer membrane having a selectivity that is less than the first selectivity.

Aspect 10: The method of Aspect 1, wherein step (j) comprises combining the third non-permeate stream, the water vapor permeate stream, and the first portion of the sweep gas stream to form a recycle stream.

Aspect 11: The method of Aspect 1, further comprising:
(k) controlling a flow split between the first portion of the sweep gas stream from the sweep gas stream.

Aspect 12: The method of Aspect 1, wherein the second non-permeate stream comprises CO2 within a range between about 0.5% and about 5%.

Aspect 13: A system comprising:
(a) a compressor for compressing a feed gas stream to form a pressurized feed gas stream, the pressurized feed gas stream comprising CH4 and being fully saturated with water;
(b) a chiller for cooling the pressurized feed gas stream to a target operating temperature of between 0 and 20 degrees C. to form a condensed water stream and a saturated gas stream;
(c) at least one membrane dryer, each of the at least one membrane dryer having a high pressure side and a low pressure side, the high pressure side extending from a feed port to a non-permeate port, the low pressure side being in fluid flow communication with a sweep port and a permeate port; the at least one membrane dryer provided for separating the saturated gas stream to form a dried gas stream and a water vapor stream, and for sweeping and discharging the water vapor stream from the low pressure side using a sweep gas stream, the dried gas stream having a water content of less than 2000 ppm;
(d) a first separation stage for separating the dried gas stream into a first non-permeate stream and a first permeate stream, the first non-permeate stream having a greater percentage of methane than the first permeate stream, the first separation stage comprising at least one first stage membrane module;
(e) a second separation stage for separating the first non-permeate stream into a second non-permeate stream and the sweep gas stream, the second non-permeate stream having a greater percentage of methane than the sweep gas stream, the second separation stage comprising at least one second stage membrane module;
(f) a third separation stage for separating the first permeate stream into a third non-permeate stream and a third permeate stream, the third non-permeate stream having a greater percentage of methane than the third permeate stream, the third separation stage comprising at least one third stage membrane module; and,
(g) a first mixing junction for combining the third non-permeate stream with the water vapor stream to form a recycle stream to be combined with the feed gas stream.

Aspect 14: The system of Aspect 13, additionally comprising a second mixing junction for optionally combining a first portion of the sweep gas stream with the third non-permeate stream.

Aspect 15: The system of Aspect 13, wherein the target operating temperature is between 3 and 7 degrees C.

Aspect 16: The system of Aspect 13, wherein the target operating temperature is approximately 5 degrees C.

Aspect 17: The system of Aspect 13, wherein the feed gas stream comprises at least 40% CH4.

Aspect 18: The system of Aspect 13, wherein the second non-permeate stream comprises CO2 within a range between about 0.5% and about 5%.

Aspect 19: The system of Aspect 13, wherein the sweep gas stream is fed in a direction of flow that is countercurrent to the direction of flow in which the saturated gas stream is fed into the at least one membrane dryer.

BRIEF DESCRIPTION OF THE DRAWING(S)

The present invention will hereinafter be described in conjunction with the appended figures wherein like numerals denote like elements.

Figure 1:
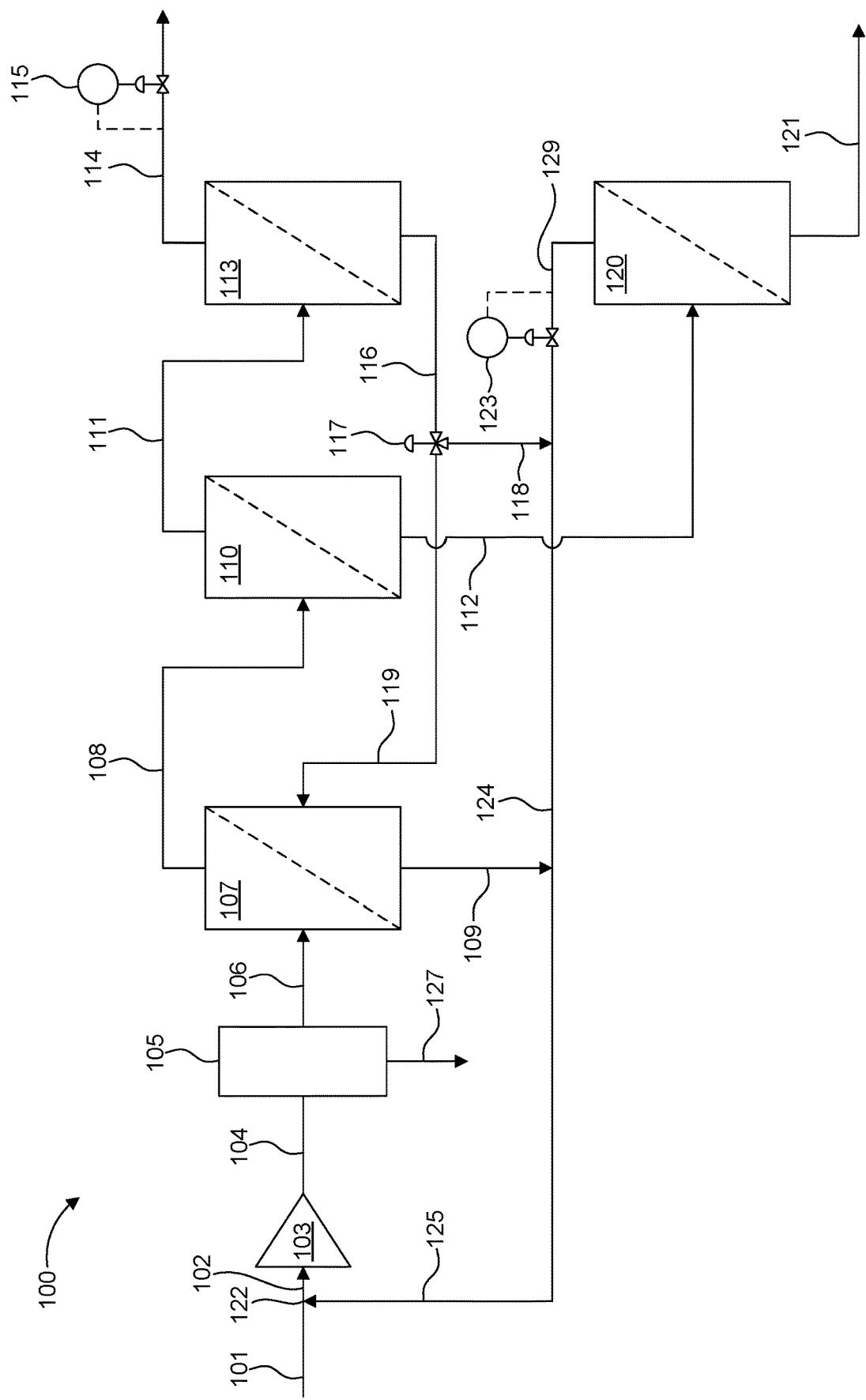
FIG. 1 is a process flow diagram of an exemplary three-stage biogas separation system.
Figure 3:
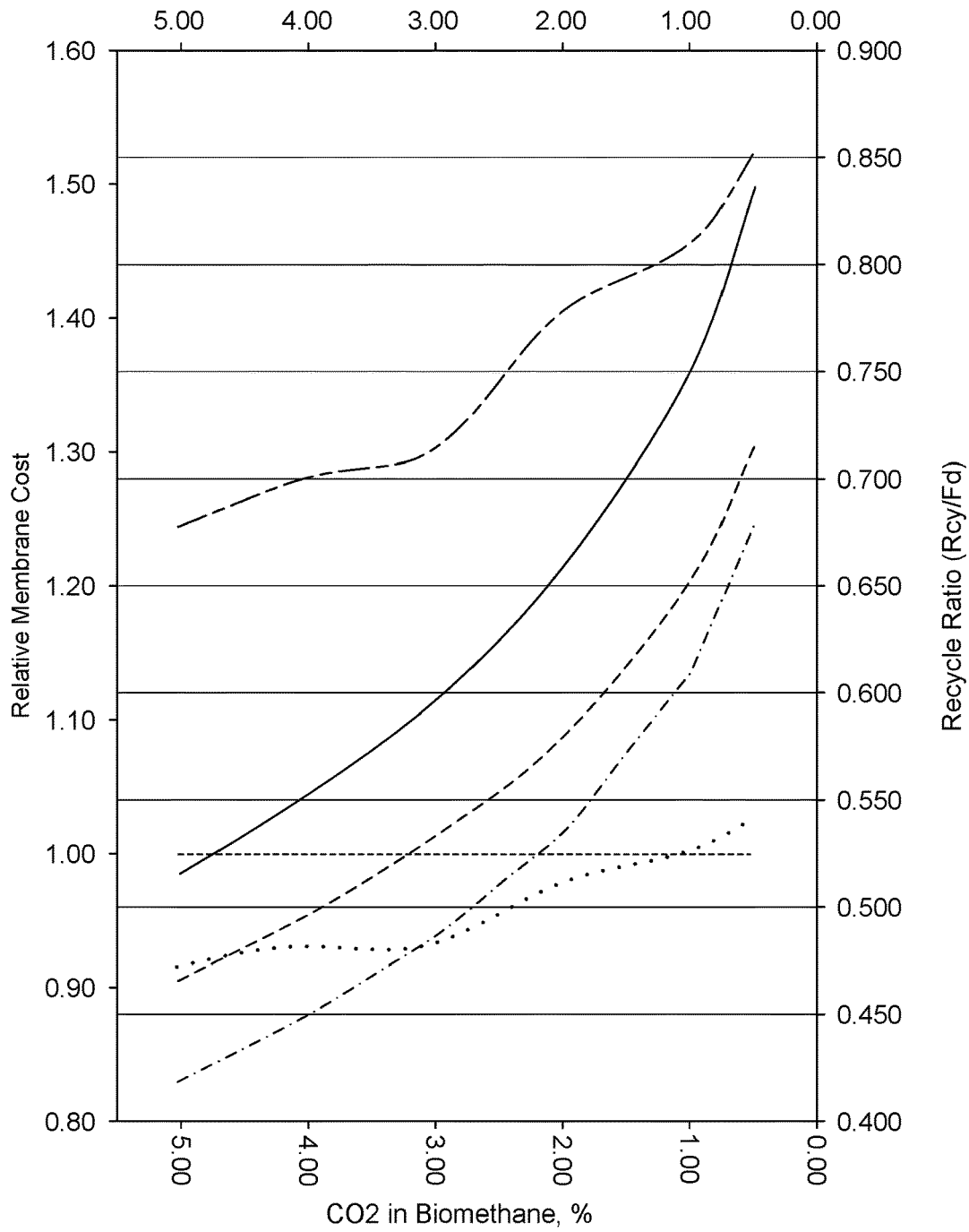
Figure 4:
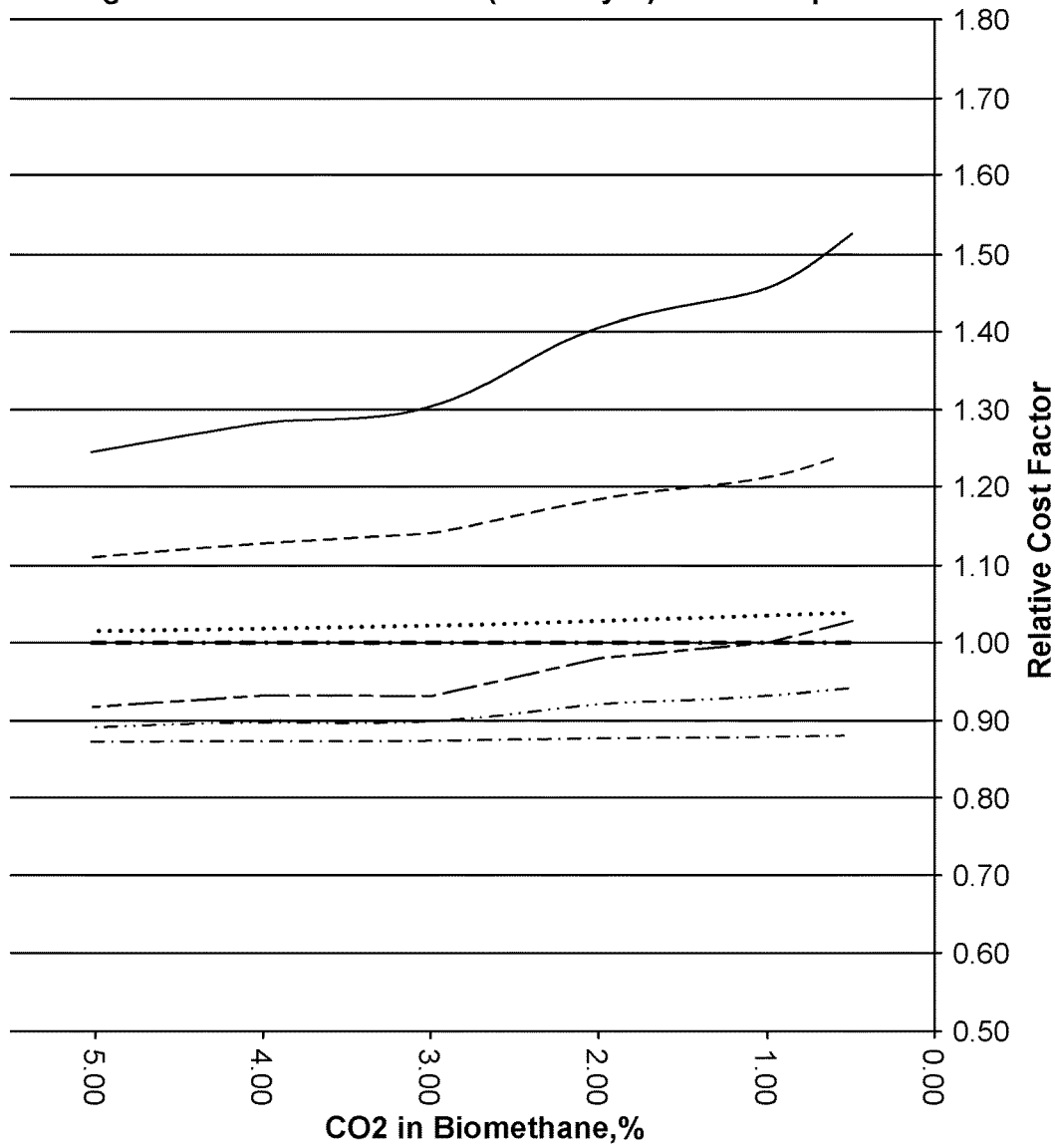

FIG. 3 is a graph setting forth the performance characteristics of the exemplary three-stage biogas separation system of FIG. 1, and comparing it with two biogas separation systems of standard design; and, FIG. 4 is a graph setting forth the relative membrane cost, relative system capital expense, and relative estimated 10-year cost of ownership of the exemplary three-stage biogas separation system of FIG. 1, when compared with two biogas separation systems of standard design.

DETAILED DESCRIPTION OF THE PREFERRED EMBODIMENTS

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing the preferred exemplary embodiments of the invention. It is understood that various changes may be made in the function and arrangement of elements without departing from the spirit and scope of the invention.

To aid in describing the invention, directional terms may be used in the specification and claims to describe portions of the present invention (e.g., upper, lower, left, right, etc.). These directional terms are merely intended to assist in describing and claiming the invention and are not intended to limit the invention in any way. In addition, reference numerals that are introduced in the specification in association with a drawing figure may be repeated in one or more subsequent figures without additional description in the specification in order to provide context for other features.

In the claims, letters are used to identify claimed steps (e.g. (a), (b), and (c)). These letters are used to aid in referring to the method steps and are not intended to indicate the order in which claimed steps are performed, unless and only to the extent that such order is specifically recited in the claims.

Unless otherwise indicated, the articles "a" and "an" as used herein mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used.

Unless otherwise stated herein, any and all percentages identified in the specification, drawings, and claims should be understood to be on a mole percentage basis. Unless otherwise stated herein, any and all pressures identified in the specification, drawings, and claims should be understood to mean gauge pressure.

The term "biogas," as used in the specification and claims, means a renewable fuel produced by the breakdown of organic matter, including without limitation food scraps and animal waste.

The term "membrane module," as used in the specification and claims, means a device that is used to selectively separate gases by flowing, at a relatively high pressure, a feed gas through one or more conduits contained within a shell (also referred to as a high pressure side). The conduits are at least partially defined by a membrane material that provides a barrier between each conduit and a shell space (also referred to as a low pressure side). The shell space is an internal volume within the shell and external to each of the membranes that is maintained at a relatively low pressure. The shell side is in fluid flow communication with a permeate port, through which gas that permeates the membrane(s) exits the shell. Optionally, a sweep port may also be provided, which supplies a sweep gas to the shell space and assists the flow of permeate gas through the permeate port. The membrane material is chosen to enable one or more gases in the feed stream to pass through the membrane material at a higher rate than other gas(es) in the feed stream. The membrane module may be of a bore-side feed design wherein the membrane module is pressurized by introduction of a feed gas stream into its bore side or may be of a shell-side feed design wherein the membrane module is pressurized by introduction of the feed gas stream into its shell side.

The term "sweep gas," as used in the specification and claims, means a stream of gas which is supplied to the low pressure side of a membrane and dilutes the concentration of the fast-permeating gas in the permeate stream, reducing its partial pressure and increasing the driving force for separation.

The term "off-gas," as used in the specification and claims, means a gas which is given off, especially one emitted as the byproduct of a chemical process.

FIG. 1 shows an exemplary embodiment of a three-stage membrane separation system 100, which includes a feed compressor 103, a chiller 105, a membrane drying stage 107, and three membrane separation stages 110, 113, and 120. A raw feed gas stream 101 typically comprises carbon dioxide ($CO_2$) and methane ($CH_4$) as major constituents, often along with other minor constituents such as oxygen ($O_2$), nitrogen ($N_2$), and water ($H_2O$). Membranes used in system 100 are typically selective for $CO_2$ over $CH_4$, meaning that $CO_2$ is considered a fast-permeating gas that preferentially crosses the membrane at a relatively high rate, while $CH_4$ is a slow permeating gas that crosses the membrane at a relatively low rate. Gas permeability through a membrane is governed by the solution-diffusion transport mechanism where the permeation rate is a function of the molecular size (diffusivity) and the molecular solubility in the polymer and is proportional to the driving force. The driving force for gas separation is the partial pressure differential of the permeating species between the high-pressure and low-pressure sides of the membrane. The gas permeability of each gaseous component of a gas mixture will typically be different, and the partial pressure of each gaseous component will be proportional to its relative concentration in the gas mixture as well as the total pressure of the gas mixture.

In system 100, a recycle stream 125 is mixed into the raw feed gas stream 101 at a mixing junction 122 to form a combined feed stream 102. The raw feed gas stream may be or comprise a biogas stream, and may be obtained from a number of sources such as a raw biogas stream resulting from a fermentation process. The raw feed gas stream may also be obtained from a landfill. A typical biogas raw feed gas stream would comprise about 40-70% $CH_4$, about 30-60% $CO_2$, would be nearly or fully saturated with water vapor, and would comprise low concentrations of hydrogen sulfide (0-5000 ppm), nitrogen (0-20%), and oxygen (0-5%). The combined feed stream 102 is compressed to a pressure that is within a range of between about 7-35 Barg in a feed compressor 103 to yield a pressurized combined feed stream 104. For example, the combined feed stream 102 may be compressed to a pressure of about 14 Barg.

The pressurized combined feed stream 104 is fed into a chiller 105 which lowers the pressurized combined feed stream 104 temperature to a target operating temperature. The target operating temperature may be between about 0- and 20-degrees C. Alternatively, the target operating temperature may be between about 3 and 7 degrees C. or about 5 degrees C. The chiller 105 may include its own refrigeration unit that cools a circulating chiller fluid or may be cooled by indirect heat exchange provided by a refrigerant. Lowering the temperature of the combined feed stream lowers the dew point at the same pressure by forming a condensed water stream 127, resulting in a chilled saturated gas stream 106. Lowering the feed temperature of the pressurized combined feed stream 104 also enables the membrane stages 110, 113, and 120 to operate with more favorable selectivity. The condensed water stream 127 may optionally be collected and drained to a condensate drain (not shown). The chilled saturated gas stream 106 is then supplied to a membrane drying stage 107, which removes water vapor from the chilled saturated gas stream 106 by selective permeation of water molecules through a polymer membrane located within the membrane drying stage 107. A suitable membrane dryer may be one such as Air Products Membrane Solutions PRISM® GreenDry Flex, which eliminates the need to heat the stream above its dewpoint.

Figure 2:
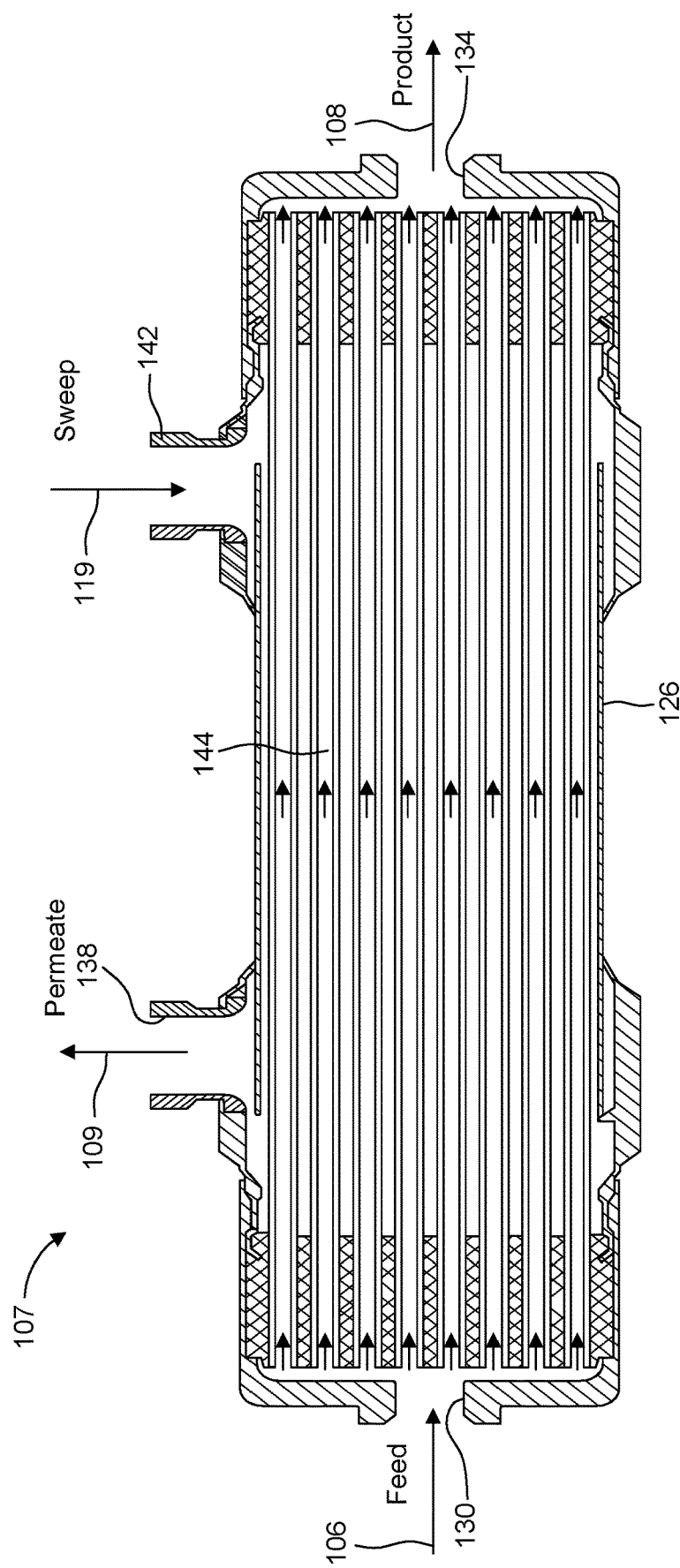
FIG. 2 is a sectional view illustrating the internal structure of the exemplary membrane drying stage.

Referring now to FIGS. 1 and 2, some of the structural details of an exemplary membrane drying stage 107 are shown. The membrane drying stage 107 comprises a generally cylindrical-shaped shell or housing 126, a feed port 130 located at a first end of the shell 126 and a non-permeate port 134 located at a second end of the shell 126 opposite the first end. The membrane drying stage 107 also includes a permeate port 138 and a sweep port 142 located along the side wall of the shell 126. In FIG. 2, the sweep port 142 is shown as being located on the same side of the shell 126 as the permeate port 138. This location is merely exemplary and the location of the sweep port 142 as shown in FIG. 2 should not be limiting. The sweep port 142 may be positioned at other locations on the shell 126. For example, the sweep port 142 may be positioned on the side of the shell 126 opposite the permeate port 138, e.g., to the right of the numeral 126 in FIG. 2, to improve sweep efficiency. Also, the length of the shell 126 as shown in FIG. 2 is merely exemplary and should not be limiting. The shell could be provided in a length that is less than that of the membrane stages 110, 113, and 120. The membrane drying stage 107 includes selectively permeable membrane fibers 144 housed within the shell 126 that serve as a molecular filter where water vapor in the chilled saturated gas stream 106 travels across a membrane faster than other gas molecules and exits the membrane drying stage through the permeate port 138 as a water vapor stream 109. The drying stage 107 must be highly selective to water in the chilled saturated gas stream 106 over other gas components. As best shown in FIG. 2, the membrane fibers 144 may consist of a bundle of hollow fibers with the ends potted in epoxy or other resin. The bundle of the membrane fibers 144 is enclosed within the shell 126 which protects the membrane and routes the gas properly.

As the chilled saturated gas stream 106 flows into the feed port 130 and along a high-pressure side (or "feed" side) of the membrane drying stage 107, the water vapor permeates through the walls of the membrane fibers 144 to a low-pressure side (or "permeate" side) and exits the membrane drying stage 107 through the permeate port 138 as the water vapor stream 109. The water vapor content of the chilled saturated gas stream 106 becomes progressively lower as the chilled saturated gas stream 106 flows along the length of the membrane drying stage 107 from the feed port 130 to the non-permeate port 134. A low pressure sweep gas stream 119 (discussed below) may be injected into the sweep port 142 to sweep the permeate side of the membrane drying stage 107 to increase the driving force for water permeation. At the opposite end, a dried gas stream 108 exits the non-permeate port 134 of the membrane drying stage 107. The dried gas stream 108 may have a water content preferably within a range of about 200-500 ppm, but also may have a water content of approximately 1000 ppm, or even approximately 2000 ppm. The effect of the membrane drying stage 107 on the composition of the dried gas stream 108 is minimal, e.g., less than 0.5 mol % change in CO2 is expected.

The dried gas stream 108 is supplied to a first membrane stage 110. A stream comprising primarily fast permeating gas permeates and exits the first membrane stage 110 as a first stage permeate stream 112. A stream comprising primarily slow permeating gases is rejected and withdrawn as a first stage non-permeate stream 111. In the case of biogas, CO2 would permeate much more rapidly than CH4. The first membrane stage 110 may include membranes exhibiting a high selectivity, but low capacity (where capacity is defined as the product of membrane permeance and active membrane area). Studies have determined that a trade-off in behavior exists between permeability and selectivity (L. M. Robeson, *J. Membr. Sci.*, 320, 390-400, 2008), which has been quantified by studying numerous polymeric membranes. It is generally known in the art that both properties cannot be simultaneously high in polymeric membranes. For example, the first membrane stage may include membranes using a polymer with a CO2 permeability between 0.5 and 3 Barrers, and a CO2/CH4 selectivity within a range of 30-60 at the target operating temperature (membrane type "A"). The first membrane stage 110 may include one or more membrane modules, with multiple membranes being arranged in series or parallel.

The first stage non-permeate stream 111 is supplied to a second membrane stage 113. The second membrane stage 113 may include membranes exhibiting high capacity but low selectivity when used at standard operating temperatures such as 30 degrees C. For example, the second membrane stage may include gas separation membranes using a polymer having a CO2 permeability between 5 and 50 Barrers, and a CO2/CH4 selectivity within a range of 20 to 30 at standard warmer operating conditions (membrane type "B"). A stream comprising primarily slow permeating gases may be rejected and withdrawn as a second stage non-permeate stream 114. The second stage non-permeate stream 114 may be withdrawn from the system 100 utilizing a pressure control valve 115 as a final product stream. A stream comprising primarily fast permeating gases permeates and exits the second membrane stage 113 as a second stage permeate stream 116. A portion of the second stage permeate stream 116 may be returned to the membrane drying stage 107 and utilized as the low pressure sweep gas stream 119. A control valve 117 may be provided to control the flow of the low pressure sweep gas stream 119 into the sweep port 142. The remaining portion of the second stage permeate stream 118 may be returned to a point upstream of the feed compressor 103 to be recycled through the system. The second membrane stage 113 may include one or more membrane modules, with multiple membranes being arranged in series or parallel.

The first stage permeate stream 112 may be supplied to a third membrane stage 120. The third membrane stage 120 serves as the final step for collecting methane, so it is important to include membranes in this stage that are highly selective. In systems of conventional design, such highly selective membranes usually also have low capacity, thus requiring a large membrane count (number of membranes) in the third membrane stage 120. In the exemplary embodiment of the present invention, however, due to lower operating temperatures, a membrane type exhibiting high capacity, typically low selectivity, and also a low CO2 activation energy may be substituted for the membrane exhibiting high selectivity but low capacity. For example, the third membrane stage 120 may include gas separation membranes of membrane type "B" having a CO2 activation energy within a range of about 1000 to 3000 cal/mol and a CH4 activation energy about 5000 cal/mol. This membrane type responds well to a lower operating temperature to achieve a higher selectivity, while substantially maintaining capacity as if operating at a higher temperature. This favorable response to low temperature can only occur if the CO2 activation energy is low and the CH4 activation energy is high. Thus, the number and cost of membranes utilized in the third membrane stage 120 can be substantially reduced. Moreover, the recycle/feed ratio can be substantially reduced thus decreasing the flow rate of the recycle stream 125 and increasing overall process efficiency. A stream comprising primarily fast permeating gases permeates the membrane and exits the third membrane stage 120 as a third stage permeate stream 121 which may be a vented stream or waste stream. A stream comprising primarily slow permeating gases may be withdrawn as a third stage non-permeate stream 129. The third stage non-permeate stream 129 exits the third membrane stage 120 via a pressure control valve 123 and may be combined with the remaining portion of the second stage permeate stream 118 and the water vapor stream 109 into a single recycle stream 125 and returned to a point upstream of the feed compressor 103 to be recycled through the system 100. The third stage non-permeate stream 129 has a higher concentration of $CO_2$ than $CH_4$ because the third membrane stage 120 is being fed with the first stage permeate stream 112, which comprises 90-95 mol % $CO_2$. The third membrane stage 120 may contain one or more membranes, with multiple membranes being arranged in series or parallel.

Referring now to FIG. 3 and Table 1, FIG. 3 is a graph showing modeled performance curves of two "standard design" (identified as "Standard Design A" and "Standard Design B") biogas separation systems (i.e., without a membrane drying stage stage) operated at 20 degrees C., and the biogas separation system 100 of the present invention ("New Design") including the membrane drying stage 107 and operated at 5 degrees C. The Standard Design A is a system of conventional design including a first membrane stage comprising membranes of type "A" (high selectivity/low capacity), a second membrane stage comprising membranes of type "B" (low selectivity/high capacity), and a third membrane stage having membranes of type "A" (high selectivity/low capacity). The Standard Design B is also of conventional design wherein all three membrane stages include membranes of type "A" (high selectivity/low capacity). All of the simulations were performed using the following operating parameters: a feed gas composition of 60% $CH_4$ and 40% $CO_2$ on a dry basis that is saturated with water vapor, the feed gas stream being compressed by the feed compressor 103 to a pressure of 14 Barg, and the feed gas stream being supplied at a flow rate of 1000 normal cubic meters per hour (ncmh). The target $CH_4$ recovery for the system was 99.5%, where $CH_4$ recovery is defined as the amount of methane in the product stream (in system 100, the second stage non-permeate stream 114) divided by the amount of methane in the feed gas stream (in system 100, the raw feed gas stream 101). Each of the simulated systems includes two curves on the graph. The first curve for each simulated system shows the membrane cost factor. The membrane cost factor for Standard Design A has been normalized to a value of 1.00 to enable comparison with the membrane cost factor for the Standard Design B and the membrane cost factor for the biogas separation system 100 of the present invention. FIG. 3 demonstrates that the New Design achieves the 99.5% $CH_4$ target product recovery while lowering the relative membrane cost for most of the $CO_2$ percentages in the product gas stream when compared with Standard Design A and for all of the $CO_2$ percentages in the product gas stream when compared with Standard Design B. The membrane costs are also set forth in Table 1 below.

The second curve for each simulated system is the applicable recycle/feed ratio (recycle stream 125 to feed gas stream 101 ratio) as a function of product gas purity (e.g., % $CO_2$ in the second stage non-permeate stream 114). As shown in FIG. 3 and in Table 1 below, by lowering the target operating temperature, the New Design achieves the 99.5% $CH_4$ target product recovery while reducing recycle flow (which lowers required compressor power) when compared with the standard design systems, i.e., Standard Design A and Standard Design B. In addition, the lower operating temperature of the New Design allows for increased use of high-capacity polymer membranes having low $CO_2$ activation energy in the membrane separation stages. When operated at lower temperature, the high-capacity membranes gained selectivity, and unexpectedly sacrificed very little capacity. The recycle/feed ratios are also set forth in Table 1.

Referring now to FIG. 4 and Table 1, the membrane cost, system capital expense, and estimated 10-year cost of ownership are provided for the Standard Design A, the Standard Design B, and the New Design for different $CO_2$ percentages in the product gas stream (second stage non-permeate stream 114). These cost and expense values have been normalized to a value of 1.00 for the Standard Design A to enable comparison with the performance of Standard Design B and the biogas separation system 100. Normalizing is achieved by dividing each value for the system 100 and for the Standard Design B by the corresponding value from the Standard Design A which is the reference so that the values for the New Design and the Standard Design B are expressed as a factor of the corresponding values for the Standard Design A. FIG. 4 and Table 1 demonstrate that by lowering the target operating temperature, the New Design achieves the 99.5% $CH_4$ target product recovery while lowering membrane cost for most $CO_2$ percentages in the product gas stream. Also, by lowering the target operating temperature, the New Design system achieves the 99.5% $CH_4$ target product recovery while achieving a lower capital expense (including capital costs for all equipment) when compared with either of the Standard Design systems. This is due to the reduction in recycle/feed ratio without an increase in membrane cost. FIG. 4 also shows a modeled 10-year cost of ownership of an exemplary implementation of the New Design system versus the two Standard Design systems for different $CO_2$ percentages in the product gas stream (second stage non-permeate stream 114). As demonstrated by FIG. 4, the New Design system provides a substantially lower expected cost of ownership over a ten-year expected life of the system than either of the Standard Design systems. As energy costs continue to rise, it is expected that the biogas separation system of the present invention will further reduce relative operating expenses.

TABLE 1

| | % $CO_2$ in Product Gas Stream | Recycle/ Feed Ratio | Relative Membrane Cost Normalized to Standard Design A | Relative System Capex | Relative System Cost (10 yr capex + opex) |
|---|---|---|---|---|---|
| Standard Design A (ABA) Operating temperature: 20° C. | 5.0 | 0.516 | 1 | 1 | 1 |
| | 4.0 | 0.553 | 1 | 1 | 1 |
| | 3.0 | 0.597 | 1 | 1 | 1 |
| | 2.0 | 0.659 | 1 | 1 | 1 |
| | 1.0 | 0.751 | 1 | 1 | 1 |
| | 0.5 | 0.835 | 1 | 1 | 1 |
| Standard Design B (AAA) Operating temperature: 20° C. | 5.0 | 0.466 | 1.25 | 1.11 | 1.02 |
| | 4.0 | 0.496 | 1.28 | 1.13 | 1.02 |
| | 3.0 | 0.533 | 1.30 | 1.14 | 1.02 |
| | 2.0 | 0.579 | 1.41 | 1.19 | 1.03 |
| | 1.0 | 0.652 | 1.46 | 1.21 | 1.03 |
| | 0.5 | 0.716 | 1.52 | 1.24 | 1.04 |
| New Design Biogas separation system 100 (ABB) Operating temperature: 5° C. | 5.0 | 0.419 | 0.92 | 0.89 | 0.87 |
| | 4.0 | 0.449 | 0.93 | 0.90 | 0.87 |
| | 3.0 | 0.486 | 0.93 | 0.90 | 0.87 |
| | 2.0 | 0.535 | 0.98 | 0.92 | 0.88 |
| | 1.0 | 0.609 | 1.00 | 0.93 | 0.88 |
| | 0.50 | 0.678 | 1.03 | 0.94 | 0.88 |

An invention has been disclosed herein in terms of preferred embodiments and alternate embodiments thereof. Of course, various changes, modifications, and alterations from the teachings of the present invention may be contemplated by those skilled in the art without departing from the intended spirit and scope thereof. It is intended that the present invention only be limited by the terms of the appended claims.

The invention claimed is:

1. A method comprising:
   (a) compressing a feed gas stream to form a pressurized feed gas stream, the pressurized feed gas stream comprising CH4 and being fully saturated with water;
   (b) cooling the pressurized feed gas stream in a chiller to a target operating temperature to form a condensed water stream and a saturated gas stream;
   (c) feeding the saturated gas stream to at least one membrane drying stage, each of the at least one membrane drying stage having a high pressure side and a low pressure side, the high pressure side extending from a feed port to a non-permeate port, the low pressure side being in fluid flow communication with a sweep port and a permeate port;
   (d) separating the saturated gas stream in the at least one membrane drying stage to form a water vapor permeate stream and a dried gas stream, the dried gas stream having a water content of less than 2000 ppm;
   (e) sweeping and discharging the water vapor permeate stream from the low pressure side using a sweep gas stream that is fed in a direction of flow that is countercurrent to the direction of flow of the saturated gas stream fed into the at least one membrane drying stage in step (c);
   (f) separating the dried gas stream in a first separation stage into a first non-permeate stream and a first permeate stream, the first non-permeate stream having a greater percentage of methane than the first permeate stream, the first separation stage comprising at least one first stage membrane module;
   (g) separating the first non-permeate stream in a second separation stage into a second non-permeate stream and the sweep gas stream, the second non-permeate stream having a greater percentage of methane than the sweep gas stream, the second separation stage comprising at least one second stage membrane module;
   (h) separating the first permeate stream in a third separation stage into a third non-permeate stream and a third permeate stream, the third non-permeate stream having a greater percentage of methane than the third permeate stream, the third separation stage comprising at least one third stage membrane module;
   (i) combining the third non-permeate stream and the water vapor permeate stream, and, optionally, a first portion of the sweep gas stream to form a recycle stream; and
   (j) combining the recycle stream with the feed gas stream before performing step (a);
   wherein the target operating temperature is between 0 and 20 degrees C.

2. The method of claim 1, wherein the target operating temperature is between 3 and 7 degrees C.

3. The method of claim 1, wherein the target operating temperature is about 5 degrees C.

4. The method of claim 1, wherein the feed gas stream comprises at least 40% CH4.

5. The method of claim 1, wherein each of the at least one first stage membrane module has a first stage CO2/CH4 selectivity that is greater than a second stage CO2/CH4 selectivity of each of the at least one second stage membrane module and a third stage CO2/CH4 selectivity of each of the at least one third stage membrane module.

6. The method of claim 1, wherein each of the at least one first stage membrane module has a first stage CO2/CH4 selectivity greater than 30 at the target operating temperature.

7. The method of claim 1, wherein each of the at least one second stage membrane module has a CO2/CH4 selectivity greater than 20 at the target operating temperature.

8. The method of claim 1, wherein each of the at least one first stage membrane module comprises a polymer membrane having a first capacity, and wherein each of the at least one second stage membrane module and each of the at least one third stage membrane module comprises a polymer membrane having a capacity that is greater than the first capacity.

9. The method of claim 1, wherein each of the at least one first stage membrane module comprises a polymer membrane having a first selectivity, and wherein each of the at least one second stage membrane module and each of the at least one third stage membrane module comprises a polymer membrane having a selectivity that is less than the first selectivity.

10. The method of claim 1, wherein step (j) comprises combining the third non-permeate stream, the water vapor permeate stream, and the first portion of the sweep gas stream to form a recycle stream.

11. The method of claim 1, further comprising:
    (k) controlling a flow split between the first portion of the sweep gas stream from the sweep gas stream.

12. The method of claim 1, wherein the second non-permeate stream comprises CO2 within a range between about 0.5% and about 5%.

* * * * *